United States Patent [19]
Adorján et al.

[11] Patent Number: 4,704,105
[45] Date of Patent: Nov. 3, 1987

[54] DISPOSABLE PLASTIC SYRINGE FOR MEDICAL USE AND PLASTIC BARREL, ESPECIALLY FOR DISPOSABLE SYRINGES

[75] Inventors: András Adorján; Csaba Dávid, both of Budapest, Hungary

[73] Assignee: Központi Váltó -és Hitelbank Rt. Innovációs Alap, Budapest, Hungary

[21] Appl. No.: 866,989

[22] PCT Filed: Dec. 5, 1983

[86] PCT No.: PCT/HU83/00060
§ 371 Date: Aug. 6, 1984
§ 102(e) Date: Aug. 6, 1984

[87] PCT Pub. No.: WO84/02278
PCT Pub. Date: Jun. 21, 1984

Related U.S. Application Data
[63] Continuation of Ser. No. 641,969, Aug. 6, 1984, abandoned.

[30] Foreign Application Priority Data
Dec. 10, 1982 [HU] Hungary .............................. 3989/82

[51] Int. Cl.$^4$ .............................................. A61M 5/00
[52] U.S. Cl. .................................... 604/222; 604/221; 604/228
[58] Field of Search ............... 604/228, 110, 199, 218, 604/221, 229, 230, 256; 128/77 Z

[56] References Cited

U.S. PATENT DOCUMENTS

| | | | |
|---|---|---|---|
| 935,415 | 9/1909 | Sands | 604/218 |
| 1,482,999 | 2/1924 | Kohnen | 604/218 |
| 2,072,327 | 3/1937 | Friedman et al. | 604/228 |
| 2,709,433 | 5/1955 | Sorenson | 604/236 |
| 2,771,880 | 1/1953 | Gotthart | 604/221 |
| 3,828,778 | 8/1974 | Weinhart | 604/228 |
| 3,874,383 | 4/1975 | Glowacki | 604/110 |
| 4,181,549 | 1/1980 | McPhee | 604/236 |
| 4,281,653 | 8/1981 | Barta et al. | 604/240 |
| 4,325,387 | 4/1982 | Helfer | 128/772 |
| 4,578,055 | 3/1986 | Fischer | 604/3 |

FOREIGN PATENT DOCUMENTS

0422444  1/1935  United Kingdom .............. 604/236

Primary Examiner—Stephen C. Pellegrino

[57] ABSTRACT

Disposable syringe made of plastics, for medical purposes, consisting of a barrel (1), a piston (2) provided with a plunger shaft (3) guided at a distance from the barrel wall, and a closure cap (4), the piston (2) being releasably joined to the plunger shaft (3). The piston (2) is at least partially softly resilient due to the fact that on the piston periphery wall parts of greatly reduced wall thickness are present. The closure cap (4) contains a sufficiently long, stable slide bearing for the plunger shaft (3), so that deformation of the latter, arising out of off-center application of force in the retracted piston position, and out of the tendency of the relatively thin plunger shaft (3) to bow or buckle, will not be transferred to the piston (2).

1 Claim, 5 Drawing Figures

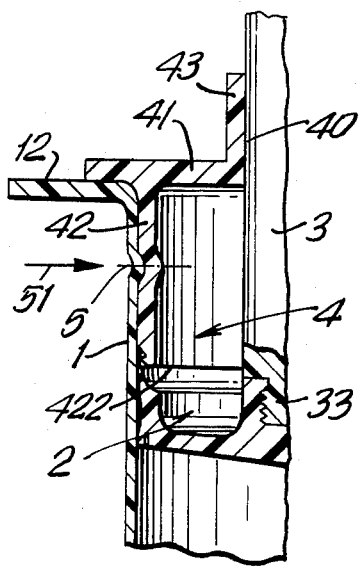
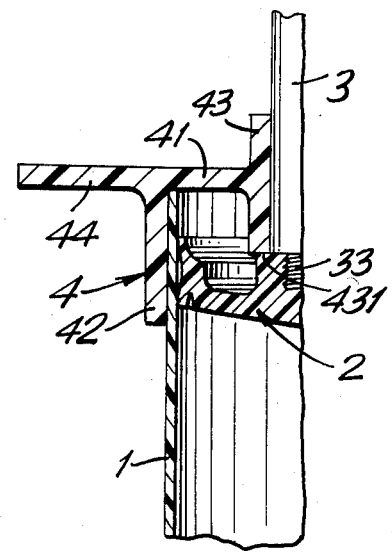
FIG.3  FIG.4
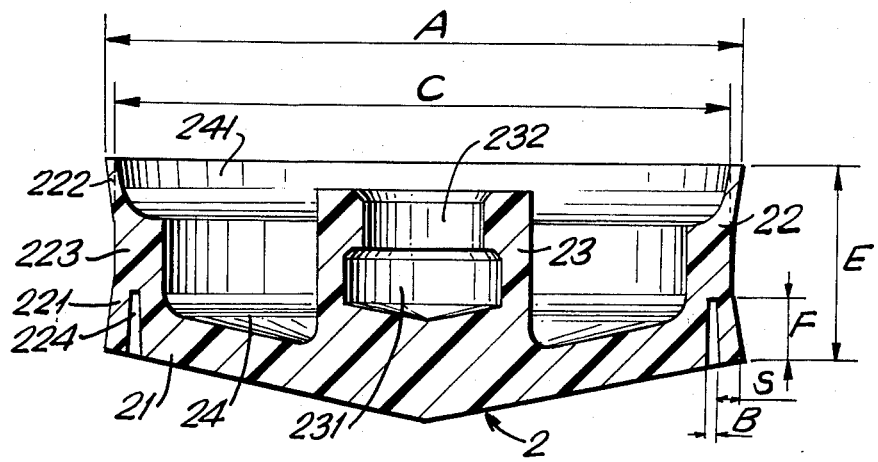
FIG.5

DISPOSABLE PLASTIC SYRINGE FOR MEDICAL USE AND PLASTIC BARREL, ESPECIALLY FOR DISPOSABLE SYRINGES

This application is a continuation of application Ser. No. 641,969, filed Aug. 6, 1984, now abondoned.

TECHNICAL FIELD OF THE INVENTION

The invention relates to a disposable syringe made of plastics, for medical purposes, consisting of a piston provided with a plunger shaft and a barrel provided at the bottom with a tapered chuck for the attachment of a cannula needle, in which the plunger shaft is guided in the barrel at a distance from the barrel wall, and the piston is releasably attached to the plunger shaft. The invention furthermore relates to a piston of thermoplastic, preferably of polyethylene, especially for disposable syringes of the above kind.

DESCRIPTION OF THE STATE OF THE ART

Disposable syringes, especially so-called two-piece disposable syringes of plastic, have long been known and widely used, which are injection-molded, assembled, sterilized and packed at low cost by modern manufacturing methods. Known disposable syringes of this kind have a plunger shaft having, as a rule, stiffening fins running offset at 90 degrees, which are guided along their edges on the inside wall of the barrel. Since in this case it is hardly avoidable that, especially when several liquids are aspirated and the indrawn air is ejected, the fins will be touched by the hand, pick up germs and transfer them to the inside wall of the barrel it has been proposed to construct disposable syringes of plastics such that the plunger shaft will be guided at a distance from the barrel wall, i.e., the largest cross-sectional dimension of the plunger shaft will be substantially smaller than the inside diameter of the barrel. This, however, creates the necessity of providing also for a centering of the plunger shaft at the plunger-shaft end of the otherwise open barrel. One known method of doing this is described in German Offenlegungsschrift No. 25 41 043. In this, two infolding projections having very thin film hinges are integrally injection molded, which, in the folded state, after the plunger has already been inserted into the barrel, produce a centering of the plunger shaft on the stroke axis by means of appropriate cutouts. One deficiency of this known solution, however, is that such syringes are difficult to assemble by machine, and at the same time the guidance afforded by the folded projections is only a centering, not a proper guidance path for the plunger shaft so as to prevent the buckling of the shaft now weakened in cross section, when an injection is given. In disposable syringes of this contamination-free kind, in which extremely slender plunger shafts are sought after with good reason, it has been found in practice to be disadvantageous that, when thin needles and especially when liquids of higher viscosity are injected, the thin plunger shaft can easily bow or buckle, and this deflection is transmitted on the one hand to the piston itself, creating sealing troubles and difficulty of movement, and on the other hand, in the fully retracted or drawn-back state of the plunger shaft the so-called starting force becomes too high, and in extreme cases the plunger shaft can even break. This is especially the case with known plastic disposable syringes in which a hard plunger of stable shape is used in combination with a relatively flexible, i.e., easily deformable, barrel. For there is a natural trend among syringe manufacturers to make the plunger shaft stiffer by selecting harder materials. In types, however, in which the piston and plunger shaft are a single injection molding of all the same material, the piston is also stiff and stable in shape, which always causes poor sealing as a source of danger. The last-named disadvantage is eliminated in known, so-called three-piece syringes by providing a substantially hard piston with a separate gasket of rubber, preferably silicone rubber. To improve the sliding and sealing properties, especially in gaskets of cheaper, silicone-free rubber, a silicone-containing wetting agent is used in the assembly of the disposable syringe. Such known disposable syringes, however, suffer from the disadvantage that on the one hand they are expensive and on the other hand the piston tends to seize in the barrel, especially after long storage. In addition, the proportioning of the wetting agent presents difficulties and an additional expense, plus sterility problems, together with chemical reaction tendencies in the case of certain injectables.

In order to be able to satisfy the complex requirements, as seen from the above statements, which injection syringes for medical purposes must meet, in the case of disposable plastic syringes, which of course are throwaway products intended for a single use, it was first recognized that the creation and use of an at least partially softly resilient piston consisting of a thermoplastic, especially polyethylene, offers the optimum approach to a solution of a considerable number of these requirements. This is because, first, a sufficiently rigid barrel can be used, which offers obvious advantages both in manufacture and in practical use. The knowledge of joining piston and plunger shaft tightly yet releasably to one another is known from the description of German Gebrauchsmuster No. 75 40 567. Thus it was also possible to provide a piston and plunger shaft made of different plastics. Now, the problem to which the present invention is addressed is to create a disposable syringe of the above-subject kind which will be largely contaminationfree, and therefore will have a very slender plunger shaft in comparison to the barrel diameter, which, with particular regard to low starting force and good sliding properties along the full stroke length, combined with uniform, good sealing action, will be equal to, or very closely approach, the practical qualities of syringes made for repeated use, while at the same time remaining low in cost.

The invention, to this end, is based on the knowledge that, by creating a sufficiently reliable guidance for the plunger shaft, the buckling or bowing tendency of the latter can be substantially reduced, even in the case of slender plunger shafts, while at the same time the guidance must be made as unyielding as possible so as to isolate the piston, which in accordance with the invention is of softly resilient material to satisfy the abovedescribed requirements, from deformations of the plunger shaft such as often occur in practice, especially when an off-center force is applied to the fully drawn-back or retracted plunger shaft.

SUMMARY OF THE INVENTION

The proposed problem is solved in accordance with the invention by a disposable syringe of the kind described above, in which, in accordance with the invention, the piston is made in the form of an at least partially softly resilient molding, preferably of polyethylene, without any separate, additional gasket of rubber, and the open end of the barrel at the plunger shaft is closed by a cap containing a sufficiently long slide bearing of stable shape for the plunger shaft passing through it. It is desirable for the length of the slide bearing, measured in the axial direction, to be at least equal to the maximum cross sectional dimension of the plunger shaft, i.e., for at least a slide bearing referred to in general mechanical design as an "over-square" bearing, which in itself assures a non-sticking sliding movement of the guided part, to be provided in disposable syringes. It is to be noted that the plunger shaft does not have to have a circular cross section, since in the injection-molding art, slide bearings of virtually any cross-sectional shape adapted to the shape of the plunger shaft as regards profile and dimensions can be made without difficulty.

In advantageous embodiments of the disposable syringe of the invention, the closure cap is integrally injectionmolded as a disk bearing two coaxial, substantially cylindrical collars, the inner collar containing the slide bearing for the plunger shaft, and the outer collar being adapted to provide a sufficiently strong force-fitting and/or positively locking connection between the closure cap and the barrel.

In an especially advantageous development of the invention, the inner collar containing the sufficiently long slide bearing for the plunger shaft and the outer collar in the form of a cylindrical wall are integrally molded in the form of coaxial collars extending from the disk in opposite axial directions from one another. In this manner, it is possible on the one hand to locate the slide bearing as closely as possible to the point of application of force in the fully retracted, critical end position of the piston, i.e., in the position in which the injection process begins, which is advantageous with regard to the desired prevention of the bowing of the plunger shaft. On the other hand, it was found to be a surprising additional advantage that in this manner an enhanced protection is provided against possible contamination of the plunger shaft during aspiration, since the outwardly projecting inner collar provides absolutely reliable protection of the shaft against contact with the operator's finger which rests on the cap during aspiration. The inner ring or collar can project axially on both sides of the disk, thereby providing a slide bearing of maximum length.

Especially with an eye to the simple machine assembly, i.e., automatic assembly, of the syringes of the invention it has been found advantageous for the cylindrical outer collar of the closure cap to be force-fitted at its outer periphery into the open, plunger-shaft end of the barrel. Since, in the opinion of physicians, it greatly improves the practical properties of a disposable syringe if the piston has a definite end stop in its retracted end position, the circular end face of the outer collar in the above embodiments is designed simultaneously as a stop for the retracted piston.

In other variant embodiments, the annular outer collar of the closure cap can be force-fitted or screw-threaded onto the plunger-shaft end of the barrel. Particularly the latter form of embodiment makes it possible to use the subject disposable syringe also as a blood sampling and blood carrying device, since in this case a full-length, smooth inner barrel wall makes it possible easily to empty the barrel contents after separation in a centrifuge; also, the closure cap is easily removable together with the plunger. In this case, the piston-facing end face of the inner collar designed as a slide bearing for the plunger shaft in accordance with the invention can simultaneously serve as a stop for the piston in the latter's fully retracted end position.

If the closure cap is, as already mentioned, force-fitted to the barrel, it can be advantageous in certain embodiments if the force fit between the barrel and the annular outer collar of the closure cap is reinforced by an interlocking means, especially by at least one permanent local deformation of the surfaces in contact, in the form, for example, of two diametrically opposite indentations produced by means of heated tools provided for the purpose in an appropriate phase of the assembly process.

As already mentioned above, the approach to the disposable syringe of the invention is based on a preliminary decision according to which the subject syringe is to be equipped with a piston of a thermoplastic which is at least partially softly resilient and thus has a good sealing action without additional rubber gasketing, combined with excellent sliding qualities. For this purpose a piston has been created by the invention, which consists preferably of polyethylene of a hardness between 65 and 90 degrees Shore, and is in the form of a substantially bell-like rotational body having an annular wall-like piston periphery formed on the piston face and having a shank portion formed centrally in the piston interior, and having an annular groove-like recess in the back of the piston between the piston periphery and the shank portion, the piston periphery having softly resilient wall portions of greatly reduced wall thickness flaring toward the piston margins in both piston marginal areas, and a cylindrical wall portion of substantially stable shape and full wall thickness being present between these wall portions. The greatly reduced wall thickness of the softly resilient wall portions in this case best amounts to 0.3 to 0.5 mm (measured at the piston margins in each case). It has been possible with the abovedescribed piston design of the invention, despite the omission of a separate gasket of rubber whose disadvantages have already been described, to achieve a reliable sealing action along the entire stroke length and in both stroke directions, and it is also distinguished by low starting force and by extremely good sliding qualities. The piston can be mass-produced from plastic by known methods and at low cost, and it requires no wetting agents of any kind for the attainment of its advantages. In the piston of the invention, the softly resilient wall portion of greatly reduced wall thickness in the marginal area on the front is constituted by an open annular groove let into the piston periphery from the front side, while in the piston marginal area on the floor side it is constituted by a graduated expansion of the annular groove-like recess between piston periphery and shank portion. Practical experiments have proven it to be advantageous for the width of the piston periphery measured in the axial direction to be from 5 to 7 mm, for the width of the annular groove let into the piston periphery on the front side to be 0.3 to 0.5 mm, and the depth of the annular groove to be 2 to 2.5 mm.

The piston in accordance with the invention possesses optimum properties, especially in embodiments in which the cylindrical wall portion of substantially stable shape is no more than equal in diameter to the inside diameter of the preferably thin-walled barrel sealingly guiding the piston, and the maximum diameter of the flaring softly resilient wall portions is 0.2 to 0.6 mm greater than the above-mentioned inside diameter of the cylinder.

The means for the secure yet releasable joining of a plunger shaft to the piston of the invention are preferably located in the shank portion formed centrally inside of the piston. In particular variants of embodiment, an internal screw thread, or else a preferably cylindrical cavity accessible from the back of the piston through a bore, can be present for receiving and holding a projection of the plunger shaft which can be snapped into it, depending on the kind of releasable fastening that is selected. If a snap-fastening is provided, the diameter of the cylindrical cavity in the shank portion is made larger than that of the bore, so that the cavity will be able to accommodate and securely hold a projection that is a certain amount larger than the bore.

BRIEF DESCRIPTION OF THE DRAWINGS

Other features, developments and advantages of the invention are described in detail below in conjunction with embodiments and details thereof, with the aid of the appended drawings. In the drawing.

FIG. 3 is a detail of a disposable syringe of the invention in section, in which the piston is shown in the fully retracted end position;

FIG. 4 is a detail of another embodiment of the disposable syringe of the invention in section, also shown with the piston fully retracted, and FIG. 5 is a sectional representation of a piston of the invention, made with softly resilient wall parts.

DESCRIPTION OF EMBODIMENTS OF THE INVENTION

Figure 1:
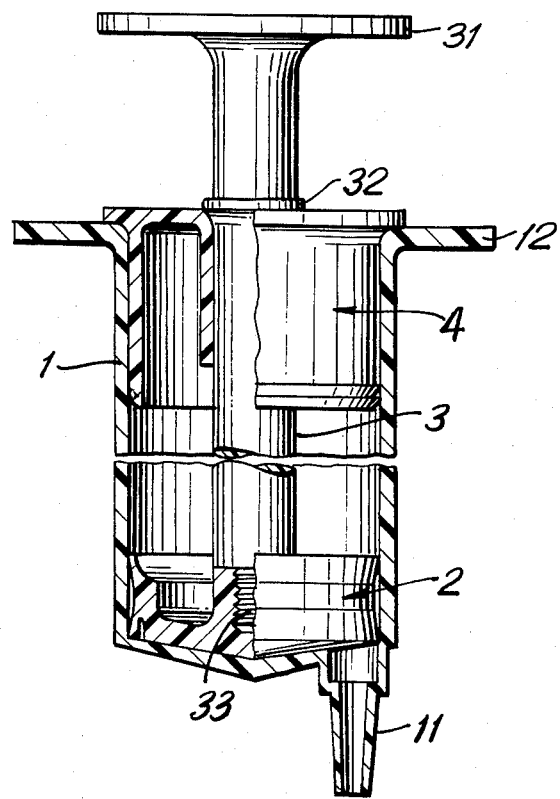
FIG. 1 is a diagrammatic longitudinal section of an embodiment of the disposable syringe of the invention, in which the piston, the plunger shaft and the closure cap are shown half in section and half in perspective.
Figure 2:
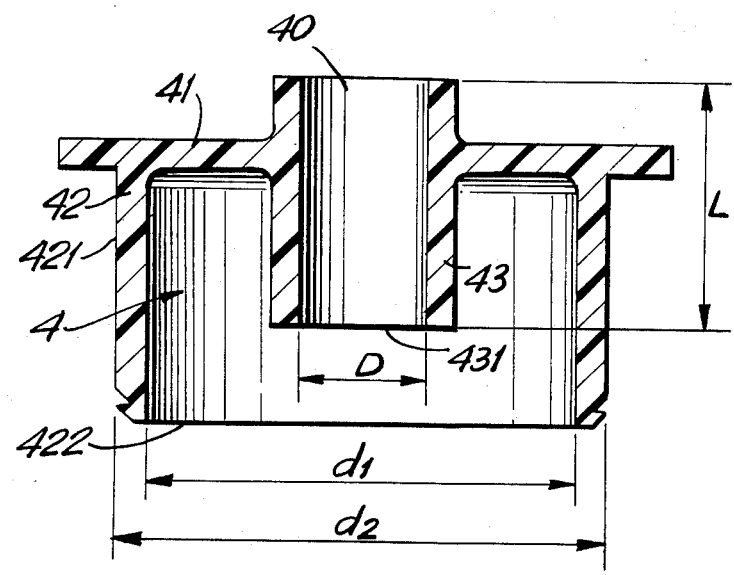
FIG. 2 is a cross section of a closure cap which contains a sufficiently long slide bearing for the plunger shaft.

FIG. 1 shows in a simplified diagrammatic longitudinal section an embodiment of the four-piece disposable injection syringe made of plastics in accordance with the invention for medical purposes, which serves only as an example. An at least partially softly resilient piston 2 made in accordance with the invention is sealingly guided in a substantially stiff-walled cylinder 1 mass-produced by the injection molding method. The barrel 1 has at its bottom end a needle chuck 11 having an internal throughbore and provided externally with a standard taper for the superimposition of a needle cannula (not shown). In the present embodiment, two diametrically opposite projections 12 serving as finger grips are formed at the open end of the barrel, which is the upper end in the drawing. The piston 2 is tightly but releasably attached to a plunger shaft 3 by a projection 33 of the plunger shaft which can be screwed into the piston. The plunger shaft 3, which is cylindrical in this case, is guided at a distance from the inner barrel wall. A slide bearing, which is formed in a closure cap 4 press-fitted into the open barrel end, serves for the stable, largely low-deformation guidance of sufficient length in the barrel chamber in accordance with the invention. The plunger shaft 3 is furthermore provided at its end remote from the piston 2 with a thumb rest 31 for convenient operation. Adjacent the thumb rest 31 there can furthermore be formed on the plunger shaft 3 an annular, circumferential bead 32 which functions as an orientation means and an aid in assembly in a manner not further discussed herein. From the illustrated construction of the disposable syringe of the invention, it is easy to see that only virgin materials, i.e., not reprocessed materials, must be used for the barrel 1 and the piston 2, since only these parts come in contact with the injectable liquid. On the other hand, reprocessed materials can easily be used for making the closure cap 4 and the plunger shaft 3. In FIG. 2 of the drawing can be seen a cross section of a closure cap 4 which contains a slide bearing 40 (of length L) which is sufficiently long in accordance with the invention, in proportion to the diameter D or to the greatest cross-sectional dimension in the case of a noncylindrical cross section of a plunger shaft (not shown here). In its most general form, the closure cap 4 is a disk 41 having two coaxial, substantially cylindrical collars 42 and 43, the inner collar 43 containing the slide bearing 40 for the plunger shaft, while the outer collar 42 is in the form of an annular wall for the purpose of a sufficiently tight frictional and/or interlocking junction between the closure cap 4 and the barrel 1. In FIG. 2 there is shown an embodiment in which the inner collar 43 projects axially from both sides of the disk 41. In all of the embodiments, it is of decisive importance that the length L of the slide bearing 40 be at least equal to the largest cross-sectional dimension, here indicated by D. Depending on the kind of appropriate design selected, either the outer periphery 421 of diameter d2 or the inner periphery of diameter d1 can be provided by the prescribed production tolerances as a force-fitting or friction-fit surface for a tight junction by permanent force fit to the inside wall or the outside wall of the open end of the cylinder 1. FIG. 3 shows an example of this, in which the outer collar 42 of the closure cap 4 is force-fitted into the open cylinder 1 provided with diametrically opposite finger grips 12. The frictional attachment is furthermore reinforced or secured by an interlocking means in the form of a local deformation 5 by an indentation made in the direction of the arrow 51. It can easily be seen in this case that the slide bearing 40 is contained in an axially outwardly projecting collar 43 on the closure cap 4, and thus not only is the deformation of the plunger shaft 3 by axial application of force, not to mention an off-center application of force, better isolated from the piston, but also the danger of contamination of the inner wall of the barrel is further reduced. Furthermore, a circular end face 422 of the outer collar 42 serves simultaneously as a defined end stop for the piston 2 in its fully retracted end position as shown. FIG. 4 shows another embodiment with the piston fully retracted. Here the closure cap is placed over the barrel end which is smooth over its full length, so that here the inside circumference of the outer collar 42 forms the high-precision surface for force-fitting onto the barrel 1. It is also possible, of course, to provide for a screw mounting of the cap by means of a screw thread. Regardless of the joining method used, two diametrically opposite projections 44 are to be formed on the closure cap 4 (instead of cylinder 1) on this kind of disposable syringes in accordance with the invention, which are usable preferably as multi-purpose instruments, also for the taking and analysis of blood samples. FIG. 4 furthermore clearly shows that in this case an end face 431 of the inner collar 43 is provided as an abutment for the piston 2 in its fully retracted end position.

Lastly, FIG. 5 shows in cross section, on an enlarged scale, a piston 2 in accordance with the invention, which is made from polyethylene of a hardness between 65 and 90 degrees Shore. The piston 2 has substantially the form of a bell-shaped rotational body. An annular piston periphery 22 is provided on the front 21 of the piston, and a central shank portion is formed inside of the piston. Between the piston periphery 22 and the shank portion 23 an annular groove-like recess 24 opening at the back of the piston is present. The piston periphery 22 has in both marginal areas softly resilient wall portions 221 and 222 of greatly reduced wall thickness S, flaring toward the piston margins. Between these thin wall portions 221 and 222 a cylindrical wall portion 223 of the full wall thickness is present, which is substantially stable in shape. In the marginal area on the front of the piston, the softly resilient wall portion 221 is represented by an open annular groove 224 let into the piston face. In the back marginal area of the piston, however, the softly resilient wall portion 222 is formed by a bevel 241 sloping from the annular groove-like recess 24. The greatly reduced wall thickness S of the softly resilient wall portions 221 and 222 is between 0.3 and 0.5 mm (measured in each case at the piston margins. The height E of the piston periphery 22 measured in the axial direction can best amount to 5 to 7 mm. The width B, measured in the plane of the piston face, of the open annular groove 224 let into the piston face is preferably between 0.3 to 0.5 mm, while the depth F of the annular groove 224 will be from 2 to 2.5 mm, depending on the piston size. The cylindrical wall portion 223 of substantially stable shape has a diameter C which is no more than equal to the inside diameter of the barrel 1 sealingly guiding the piston 2, and the maximum diameters A of the flaring softly resilient wall portions 221 and 222 are 0.2 to 0.6 mm greater than the inside diameter of the barrel 1.

In the shank portion 23 formed centrally inside of the piston, a female thread can be present, for the tight, yet releasable joining of the piston 2 to its plunger shaft 3, in the manner represented in FIG. 1. FIG. 5, however, shows another embodiment, in which a cylindrical cavity 231 is created, which is accessible from the back through a bore 232. The diameter of the cavity 231 is made larger than the diameter of the bore 232, so that a projection 33 of the plunger shaft 3, which is overdimensioned with respect to the bore diameter, can be introduced through the bore 232 with a certain force into the cavity 231, i.e., it can be snapped into it, thus providing a sufficiently tight, but releasable attachment between piston 2 and plunger shaft 3. This kind of attachment is especially desirable for the automatic assembly of the disposable syringes of the invention by machinery.

In accordance with the proposed problem, the disposable syringes equipped with pistons of the described kind in accordance with the invention, made of plastics in accordance with the present invention, are distinguished especially by the fact that their performance in use is substantially equal to that of the syringes designed for repeated use (made of glass and metal), which have long been known, and yet they can be made inexpensively as massproduced, disposable products. These advantageous characteristics are the result of the combination, in accordance with the invention, of the constructional features set forth in the present description. The disposable syringes of the present invention are virtually contamination-free, they have outstanding sealing and sliding properties combined with very low starting force, without rubber gaskets and also without wetting agents or lubricants, and all of their parts can be mass-manufactured inexpensively as low-cost plastic articles by the injection molding process. In spite of their four components, their design permits easy automatic assembly, resulting in an extensive freedom from agents of infection plus economic advantages. Another advantage is due to the fact that, as already mentioned, the closure cap and the plunger shaft can also be made from reprocessed materials.

It is easy to understand that, within the scope of protection defined by the following claims, other embodiments of the disposable syringes of the invention and of the piston can be realized within the scope of the idea of the invention.

| List of the reference numbers used | |
|---|---|
| Barrel | 1 |
| Chuck | 11 |
| (Diametral) projection | 12 |
| Piston | 2 |
| Piston face | 21 |
| Piston periphery | 22 |
| (Softly resilient) wall portion | 221, 222 |
| Wall portion | 223 |
| Annular groove | 224 |
| Shank portion | 23 |
| Cavity | 231 |
| Bore | 232 |
| Recess | 24 |
| Bevel | 241 |
| Plunger shaft | 3 |
| Thumb rest | 31 |
| Bead | 32 |
| Projection | 33 |
| Closure cap | 4 |
| Slide bearing | 40 |
| Disk | 41 |
| (Outer) collar | 42 |
| Outer circumference | 421 |
| End face | 422 |
| (Inner) collar | 43 |
| End face | 431 |
| Projection | 44 |
| (Local) deformation | 5 |
| Arrow direction | 51 |

We claim:

1. A disposable plastic syringe for medical use, comprising a substantially rigid plastic barrel having a closed end with a taper nozzle to which an injection needle of suitable size can be attached, a piston comprising a single, at least partially soft-elastic component part made of thermoplastic material disposed in direct sealing and sliding engagement with an inner wall surface of the barrel, the other end of the barrel opposite to said closed end being open, a separate closure member closing said open end; said separate closure member comprising a disc-shaped cover plate made of plastic material and having an outer substantially cylindrical ring wall and an inner substantially cylindrical ring wall, each of said ring walls protruding coaxially from said cover plate, said outer ring wall protruding in a direction towards said barrel closed end and being shaped and arranged for a durably secure fastening of said closure member to said barrel in a force-fit tight and locked manner and having a cylindrical external circumferential surface which is in a tight fit with said barrel when said closure member is inserted into said open end of said barrel, an inner wall surface of said barrel, at least one local indentation in said barrel inner wall surace and in said outer ring wall to additionally secure and strengthen the fit between said barrel and said outer ring wall; said inner ring wall protruding both in a direction towards said barrel closed end and in a direction away from said barel closed end and comprising a substantially shape-retentive positive slide guide of axially elongate tubular form, a plastic reciprocable plunger shaft connected to said piston, said plunger shaft having a maximum cross-sectional dimension which is substantially smaller than the inside diameter of said barrel and being slidable in said slide guide, the axial length of said slide guide being at least equal to the largest cross-sectional dimension of the plunger shaft and of a total length sufficient to prevent buckling or bowing of said plunger shaft, said plunger shaft being radially spaced from said barrel inner wall surface, said piston including a substantially hollow bell-shaped rotational body having a piston face and an annular wall-like piston periphery formed on said piston face, a shank portion formed centrally in the piston interior, an annular groove-like recess open rearwardly of said piston face toward said barrel open end and located between said wall-like piston periphery and said shank portion, said piston wall-like periphery having first and second softly resilient wall portions of greatly reduced wall thickness with respect to the remainder of said piston wall thickness, said softly resilient wall portions flaring toward the outer periphery of said piston, and a substantially shape-stable cylindrical wall portion of full wall thickness extending between said said first and second wall portions, an open annular groove extending into the piston body from the piston face and separating said first softly resilient wall portion from the remainder of said piston face, a sloping bevel defined in said wall-like piston periphery to be in said annular groove-like recess, said bevel being located adjacent to said second softly resilient wall portion and extending from the rearmost portion of said piston toward said piston face to said wall portion of full wall thickness and being located between said piston outer periphery and said shank portion.

* * * * *